United States Patent
Jautelat et al.

(10) Patent No.: US 6,201,128 B1
(45) Date of Patent: Mar. 13, 2001

(54) METHOD FOR PRODUCING TRIAZOLINTHION DERIVATIVES

(75) Inventors: Manfred Jautelat, Burscheid (DE); David Erdman, Liberty, MO (US)

(73) Assignee: Bayer Aktiengesellschaft, Leverkusen (DE)

(*) Notice: Subject to any disclaimer, the term of this patent is extended or adjusted under 35 U.S.C. 154(b) by 0 days.

(21) Appl. No.: 09/509,763
(22) PCT Filed: Sep. 25, 1998
(86) PCT No.: PCT/EP98/06112
  § 371 Date: Mar. 28, 2000
  § 102(e) Date: Mar. 28, 2000
(87) PCT Pub. No.: WO99/18087
  PCT Pub. Date: Apr. 15, 1999

(30) Foreign Application Priority Data

Oct. 8, 1997 (DE) ............................................... 197 44 402
Sep. 1, 1998 (DE) ............................................... 198 39 688

(51) Int. Cl.$^7$ ............................................. C07D 249/12
(52) U.S. Cl. ................................................... 548/263.2
(58) Field of Search ......................................... 548/263.2

(56) References Cited

U.S. PATENT DOCUMENTS

| | | | |
|---|---|---|---|
| 4,913,727 | 4/1990 | Stroech et al. | 297/92 |
| 4,980,488 | 12/1990 | Stroech et al. | 297/563 |
| 4,988,819 | 1/1991 | Stroech et al. | 297/267.8 |
| 4,990,677 | 2/1991 | Stroech et al. | 297/29 |
| 5,034,052 | 7/1991 | Stroech et al. | 297/92 |
| 5,856,495 | 1/1999 | Weckbecker et al. | 197/272.4 |

FOREIGN PATENT DOCUMENTS

| | | |
|---|---|---|
| 40 30 039 | 3/1992 | (DE) . |
| 196 01 189 | 7/1997 | (DE) . |
| 96/16048 | 5/1996 | (WO) . |

OTHER PUBLICATIONS

*I. Arai: Bulletin of the Chemical Society of Japan, vol. 46, No. 7, (month unavailable) 1973, pp. 2215–2218, XP002087557, cited in the application, see p. 2216, right-–hand column, reaction schema; p. 2217, left–hand column, reaction schema, p. 2218, "Experimental".

Primary Examiner—Patricia L. Morris
(74) Attorney, Agent, or Firm—Joseph C. Gil

(57) ABSTRACT

According to a novel process, triazolinethione derivatives of the formula

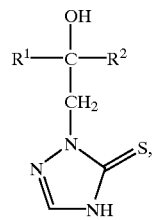
(I)

in which $R^1$ and $R^2$ are each as defined in the description, can be prepared by a) reacting hydrazine derivatives of the formula

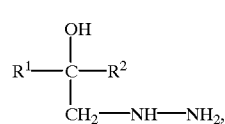
(II)

with formaldehyde and thiocyanate of the formula

X—SCN (III), in which

X represents sodium, potassium or ammonium, in the presence of a diluent and if appropriate in the presence of an acid, and b) reacting the resulting triazolidinethiones of the formula

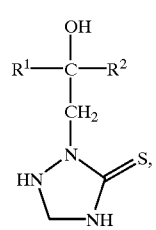
(IV)

either

α) with oxidizing agents, if appropriate in the presence of a catalyst and in the presence of a diluent, or β) with formic acid.

The triazolidinethiones of the formula (IV) are novel.

9 Claims, No Drawings

METHOD FOR PRODUCING TRIAZOLINTHION DERIVATIVES

The present invention relates to a novel process for preparing triazolinethione derivatives which are known as active compounds having microbicidal, in particular fungicidal, properties.

It is already known that triazolinethione derivatives can be prepared by either reacting the corresponding triazole derivatives successively with strong bases and sulphur and then hydrolysing them, or reacting them directly with sulphur at high temperatures, followed by treatment with water (cf. WO-A 96-16 048). However, this process has the disadvantage that the desired products are obtained in only relatively low yields, or that reaction conditions are required which are difficult to maintain on an industrial scale.

Furthermore, it has already been described that certain 1,2,4-triazoline-5-thiones substituted in the 3 position can be prepared by reacting N-chlorothioformnyl-N-(1-chloroalk-1-ene)-amines with carbonylhydrazine derivatives (cf. DE-A 197-01 032, DE-A and EP-A 0 784 053). However, the synthesis of corresponding substances which do not have a substituent in the 3 position is not mentioned.

Furthermore, Bull. Chem. Soc. Japan 46, 2215 (1973) discloses that triazolinethiones substituted in the 3 position can be synthesized by reacting phenylhydrazine with sodium thiocyanate and ketones or aldehydes in the presence of hydrochloric acid and treating the resulting triazolidinethiones substituted in the 3 position with oxidizing agents. This process has the disadvantages that very long reaction times are required and that no triazolinethiones which are unsubstituted in the 3 position can be obtained in this manner.

Finally, it is also known that 2-(1-chloro-cycloprop-1-yl)-1-(2-chloro-phenyl)-3-(1,2,4-triazol-1-yl)-propan-2-ol is obtained when [1-(2-chloro-phenyl)-2-(1-chloro-cycloprop-1-yl)-2-hydroxy]-propyl-hydrazine is reacted with formamidine acetate (cf. DE-A 40 30 039). However, thiono derivatives of triazoles are not obtainable by this method.

It has now been found that triazolinethione derivatives of the formula

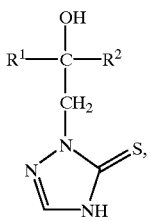

(I)

in which

R$^1$ and R$^2$ are identical or different and each represents optionally substituted alkyl, optionally substituted alkenyl, optionally substituted cycloalkyl, optionally substituted aralkyl, optionally substituted aralkenyl, optionally substituted aroxyalkyl, optionally substituted aryl or optionally substituted heteroaryl, can be prepared by a) reacting, in a first step, hydrazine derivatives of the formula

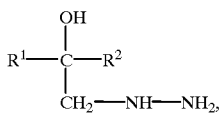

(II)

in which

R$^1$ and R$^2$ are each as defined above with formaldehyde and thiocyanate of the formula

X—SCN (III), in which

X represents sodium, potassium or ammonium, in the presence of a diluent and if appropriate in the presence of an acid, and b) reacting the resulting triazolidinethiones of the formula

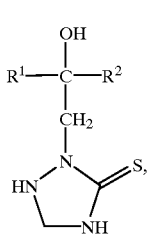

(IV)

in which

R$^1$ and R$^2$ are each as defined above in a second step either

α) with oxidizing agents, if appropriate in the presence of catalyst and in the presence of a diluent, or β) with formic acid of the formula

HCOOH (V)

It is extremely surprising that triazolinethione derivatives of the formula (I) can be prepared by the process according to the invention in substantially higher yields or under considerably simpler conditions than by the prior-art methods.

The process according to the invention has a number of advantages. Thus, as already mentioned, it makes it possible to synthesize triazolinethiones of the formula (I) in high yield. It is also favourable that the required starting materials and reaction components can be prepared in a simple manner and are available even in relatively large amounts. A further advantage consists in the fact that the individual reaction steps can be carried out and the reaction products can be isolated without any problems.

Using [1-(2-chloro-phenyl)-2-(1-chloro-cycloprop-1-yl)-2-hydroxy]-propyl-1-hydrazine as starting material and reacting this in the first step with paraformaldehyde and ammonium thiocyanate and allowing the resulting product to react in the second step with oxygen in the presence of potassium hydroxide and sulphur, the course of the process according to the invention can be illustrated by the scheme below.

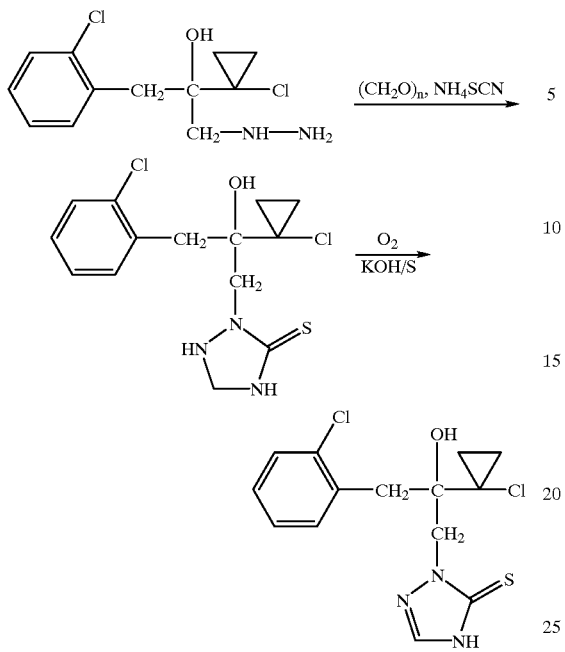

The formula (II) provides a general definition of the hydrazine derivatives required as starting materials for carrying out the process according to the invention. Preference is given to using compounds of the formula (II) in which R¹ represents straight-chain or branched alkyl having 1 to 6 carbon atoms, where these radicals may be mono- to tetrasubstituted by identical or different substituents from the group consisting of halogen, alkoxy having 1 to 4 carbon atoms, alkoximino having 1 to 4 carbon atoms in the alkoxy moiety and cycloalkyl having 3 to 7 carbon atoms, or represents straight-chain or branched alkenyl having 2 to 6 carbon atoms, where each of these radicals may be mono- to trisubstituted by identical or different substituents from the group consisting of halogen, alkoxy having 1 to 4 carbon atoms and cycloalkyl having 3 to 7 carbon atoms, or represents cycloalkyl having 3 to 7 carbon atoms, where each of these radicals may be mono- to trisubstituted by identical or different substituents from the group consisting of halogen, cyano and alkyl having 1 to 4 carbon atoms, or represents aralkyl having 6 to 10 carbon atoms in the aryl moiety and 1 to 4 carbon atoms in the straight-chain or branched alkyl moiety, where the aryl moiety may in each case be mono- to trisubstituted by identical or different substituents from the group consisting of halogen, alkyl having 1 to 4 carbon atoms, alkoxy having 1 to 4 carbon atoms, alkylthio having 1 to 4 carbon atoms, halogenalkyl having 1 or 2 carbon atoms and 1 to 5 identical or different halogen atoms, halogenoalkoxy having 1 or 2 carbon atoms and 1 to 5 identical or different halogen atoms, halogenoalkylthio having 1 or 2 carbon atoms and 1 to 5 identical or different halogen atoms, cycloalkyl having 3 to 7 carbon atoms, phenyl, phenoxy, alkoxycarbonyl having 1 to 4 carbon atoms in the alkoxy moiety, alkoximinoalkyl having 1 to 4 carbon atoms in the alkoxy moiety and 1 to 4 carbon atoms in the alkyl moiety, nitro and cyano, or represents aralkenyl having 6 to 10 carbon atoms in the aryl moiety and 2 to 4 carbon atoms in the alkenyl moiety, where the aryl moiety may in each case be mono- to trisubstituted by identical or different substituents from the group consisting of halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 identical or different halogen atoms, halogenoalkoxy having 1 or 2 carbon atoms and 1 to 5 identical or different halogen atoms, halogenoalkylthio having 1 or 2 carbon atoms and 1 to 5 identical or different halogen atoms, cycloalkyl having 3 to 7 carbon atoms, phenyl, phenoxy, alkoxycarbonyl having 1 to 4 carbon atoms in the alkoxy moiety, alkoximinoalkyl having 1 to 4 carbon atoms in the alkoxy moiety and 1 to 4 carbon atoms in the alkyl moiety, nitro and cyano, or represents aroxyalkyl having 6 to 10 carbon atoms in the aryl moiety and 1 to 4 carbon atoms in the straight-chain or branched oxyalkyl moiety, where the aryl moiety may in each case be mono- to trisubstituted by identical or different substituents from the group consisting of halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 identical or different halogen atoms, halogenoalkoxy having 1 or 2 carbon atoms and 1 to 5 identical or different halogen atoms, halogenoalkylthio having 1 or 2 carbon atoms and 1 to 5 identical or different halogen atoms, cycloalkyl having 3 to 7 carbon atoms, phenyl, phenoxy, alkoxycarbonyl having 1 to 4 carbon atoms in the alkoxy moiety, alkoximinoalkyl having 1 to 4 carbon atoms in the alkoxy moiety and 1 to 4 carbon atoms in the alkyl moiety, nitro and cyano, or represents aryl having 6 to 10 carbon atoms, where each of these radicals may be mono- to trisubstituted by identical or different substituents from the group consisting of halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 identical or different halogen atoms, halogenoalkoxy having 1 or 2 carbon atoms and 1 to 5 identical or different halogen atoms, halogenoalkylthio having 1 or 2 carbon atoms and 1 to 5 identical or different halogen atoms, cycloalkyl having 3 to 7 carbon atoms, phenyl, phenoxy, alkoxycarbonyl having 1 to 4 carbon atoms in the alkoxy moiety, alkoximinoalkyl having 1 to 4 carbon atoms in the alkoxy moiety and 1 to 4 carbon atoms in the alkyl moiety, nitro and cyano, or represents an optionally benzo-fused five- or six-membered heteroaromatic radical having 1 to 3 heteroatoms, such as nitrogen, sulphur and/or oxygen, where each of these radicals may be mono- to trisubstituted by identical or different substituents from the group consisting of halogen, alkyl having 1 to 4 carbon atoms, hydroxyalkyl having 1 to 4 carbon atoms, hydroxyalkinyl having 3 to 8 carbon atoms, alkoxy having 1 or 2 carbon atoms, alkylthio having 1 or 2 carbon atoms, halogenoalkyl, halogenoalkoxy and halogenoalkylthio having in each case 1 or 2 carbon atoms and 1 to 5 identical or different halogen atoms, such as fluorine or chlorine atoms, formyl, dialkoxymethyl having 1 or 2 carbon atoms in each alkoxy group, acyl having 2 to 4 carbon atoms, alkoxycarbonyl having 1 to 4 carbon atoms in the alkoxy moiety, alkoximinoalkyl having 1 to 4 carbon atoms in the alkoxy moiety and 1 to 3 carbon atoms in the alkyl moiety, nitro and cyano, and $R^2$ represents straight-chain or branched alkyl having 1 to 6 carbon atoms, where these radicals may be mono- to tetrasubstituted by identical or different substituents from the group consisting of halogen, alkoxy having 1 to 4 carbon atoms, alkoximino having 1 to 4 carbon atoms in the alkoxy moiety and cycloalkyl having 3 to 7 carbon atoms, or represents straight-chain or branched alkyl having 2 to 6 carbon atoms, where each of these radicals may be mono- to trisubstituted by identical or different substituents from the group consisting of halogen, alkoxy having 1 to 4 carbon atoms and cycloalkyl having 3 to 7 carbon atoms, or represents cycloalkyl having 3 to 7 carbon atoms, where each of these radicals may be mono- to trisubstituted by identical or different substituents from the group consisting of halogen, cyano and alkyl having 1 to 4 carbon atoms, or represents aralkyl having 6 to 10 carbon atoms in the aryl moiety and 1 to 4 carbon atoms in the straight-chain or branched alkyl moiety, where the aryl moiety may in each case be mono- to trisubstituted by identical or different substituents from the group consisting of halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 identical or different halogen atoms, halogenoalkoxy having 1 or 2 carbon atoms and 1 to 5 identical or different halogen atoms, halogenoalkylthio having 1 or 2 carbon atoms and 1 to 5 identical or different halogen atoms, cycloalkyl having 3 to 7 carbon atoms, phenyl, phenoxy, alkoxycarbonyl having 1 to 4 carbon atoms in the alkoxy moiety, alkoximinoalkyl having 1 to 4 carbon atoms in the alkoxy moiety and 1 to 4 carbon atoms in the alkyl moiety, nitro and cyano, or represents aralkenyl having 6 to 10 carbon atoms in the aryl moiety and 2 to 4 carbon atoms in the alkenyl moiety, where the aryl moiety may initially be mono- to trisubstituted by identical or different substituents from the group consisting of halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 identical or different halogen atoms, halogenoalkoxy having 1 or 2 carbon atoms and 1 to 5 identical or different halogen atoms, halogenoalkylthio having 1 or 2 carbon atoms and 1 to 5 identical or different halogen atoms, cycloalkyl having 3 to 7 carbon atoms, phenyl, phenoxy, alkoxycarbonyl having 1 to 4 carbon atoms in the alkoxy moiety, alkoximinoalkyl having 1 to 4 carbon atoms in the alkoxy moiety and 1 to 4 carbon atoms in the alkyl moiety, nitro and cyano, or represents aroxyalkyl having 6 to 10 carbon atoms in the aryl moiety and 1 to 4 carbon atoms in the straight-chain or branched oxyalkyl moiety, where the aryl moiety may in each case be mono- to trisubstituted by identical or different substituents from the group consisting of halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 identical or different halogen atoms, halogenoalkoxy having 1 or 2 carbon atoms and 1 to 5 identical or different halogen atoms, halogenoalkylthio having 1 or 2 carbon atoms and 1 to 5 identical or different halogen atoms, cycloalkyl having 3 to 7 carbon atoms, phenyl, phenoxy, alkoxycarbonyl having 1 to 4 carbon atoms in the alkoxy moiety, alkoximinoalkyl having 1 to 4 carbon atoms in the alkoxy moiety and 1 to 4 carbon atoms in the alkyl moiety, nitro and cyano, or represents aryl having 6 to 10 carbon atoms, where each of these radicals may be mono- to trisubstituted by identical or different substituents from the group consisting of halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 identical or different halogen atoms, halogenoalkoxy having 1 or 2 carbon atoms and 1 to 5 identical or different halogen atoms, halogenoalkylthio having 1 or 2 carbon atoms and 1 to 5 identical or different halogen atoms, cycloalkyl having 3 to 7 carbon atoms, phenyl, phenoxy, alkoxycarbonyl having 1 to 4 carbon atoms in the alkoxy moiety, alkoximinoalkyl having 1 to 4 carbon atoms in the alkoxy moiety and 1 to 4 carbon atoms in the alkyl moiety, nitro and cyano, or represents an optionally benzo-fused five- or six-membered heteroaromatic radical having 1 to 3 heteroatoms, such as nitrogen, sulphur and/or oxygen, where each of these radicals may be mono- to trisubstituted by identical or different substituents from the group consisting of halogen, alkyl having 1 to 4 carbon atoms, hydroxyalkyl having 1 to 4 carbon atoms, hydroxyalkinyl having 3 to 8 carbon atoms, alkoxy having 1 or 2 carbon atoms, alkylthio having 1 or 2 carbon atoms, halogenoalkyl, halogenoalkoxy and halogenoalkylthio having in each case 1 or 2 carbon atoms and 1 to 5 identical or different halogen atoms, such as fluorine or chlorine atoms, formyl, dialkoxymethyl having 1 or 2 carbon atoms in each alkoxy group, acyl having 2 to 4 carbon atoms, alkoxycarbonyl having 1 to 4 carbon atoms in the alkoxy moiety, alkoximinoalkyl having 1 to 4 carbon atoms in the alkoxy moiety and 1 to 3 carbon atoms in the alkyl moiety, nitro and cyano.

Particular preference is given to using hydrazine derivatives of the formula (II) in which $R^1$ represents straight-chain or branched alkyl having 1 to 4 carbon atoms, where these radicals may be mono- to tetrasubstituted by identical or different substituents from the group consisting of fluorine, chlorine, bromine, methoxy, ethoxy, propoxy, isopropoxy, alkoximino having 1 or 2 carbon atoms in the alkoxy moiety, cyclopropyl, cyclobutyl, cyclopentyl and cyclohexyl, or represents straight-chain or branched alkenyl having 2 to 5 carbon atoms, where each of these radicals may be mono- to trisubstituted by identical or different substituents from the group consisting of fluorine, chlorine, bromine, methoxy, ethoxy, propoxy, isopropoxy, cyclopropyl, cyclobutyl, cyclopentyl and cyclohexyl, or represents cycloalkyl having 3 to 6 carbon atoms, where each of these radicals may be mono- to trisubstituted by identical or different substituents from the group consisting of fluorine, chlorine, bromine, cyano, methyl, ethyl, propyl, isopropyl and tert-butyl, or represents phenylalkyl having 1 to 4 carbon atoms in the straight-chain or branched alkyl moiety, where the phenyl moiety may be mono- to trisubstituted by identical or different substituents from the group consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximninomethyl, 1-methoximinoethyl, nitro and cyano, or represents phenylalkenyl having 2 to 4 carbon atoms in the alkenyl moiety, where the phenyl moiety may be mono- to trisubstituted by identical or different substituents from the group consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximinomethyl, 1-methoximinoethyl, nitro and cyano, or represents phenoxyalkyl having 1 to 4 carbon atoms in the straight-chain or branched oxyalkyl moiety, where the phenyl moiety may be mono- to trisubstituted by identical or different substituents from the group consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximinomethyl, 1-methoximinoethyl, nitro and cyano, or represents phenyl which may be mono- to trisubstituted by identical or different substituents from the group consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximinomethyl, 1-methoximinoethyl, nitro and cyano, or represents pyrazolyl, imidazolyl, 1,2,4-triazolyl, pyrrolyl, furanyl, thienyl, thiazolyl, oxazolyl, pyridinyl, pyrimidinyl, triazinyl, quinolinyl, isoquinolinyl, quinazolinyl, indolyl, benzothienyl, benzofuranyl, benzothiazolyl or benzimidazolyl, where each of these radicals may be mono- to trisubstituted by identical or different substituents from the group consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, chlorodifluoromethylthio, hydroxymethyl, hydroxyethyl, hydroxyalkinyl having 4 to 6 carbon atoms, methoxycarbonyl, ethoxycarbonyl, methoximinomethyl, 1-methoximinoethyl, nitro, cyano, formyl, dimethoxymethyl, acetyl and propionyl, and $R^2$ represents straight-chain or branched alkyl having 1 to 4 carbon atoms, where these radicals may be mono- to tetrasubstituted by identical or different substituents from the group consisting of fluorine, chlorine, bromine, methoxy, ethoxy, propoxy, isopropoxy, alkoximino having 1 or 2 carbon atoms in the alkoxy moiety, cyclopropyl, cyclobutyl, cyclopentyl and cyclohexyl, or represents straight-chain or branched alkenyl having 2 to 5 carbon atoms, where each of these radicals may be mono- to trisubstituted by identical or different substituents from the group consisting of fluorine, chlorine, bromine, methoxy, ethoxy, propoxy, isopropoxy, cyclopropyl, cyclobutyl, cyclopentyl and cyclohexyl, or represents cycloalkyl having 3 to 6 carbon atoms, where each of these radicals may be mono- to trisubstituted by identical or different substituents from the group consisting of fluorine, chlorine, bromine, cyano, methyl, ethyl, propyl, isopropyl and tert-butyl, or represents phenylalkyl having 1 to 4 carbon atoms in the straight-clhain or branched alkyl moiety, where the phenyl moiety may be mono- to trisubstituted by identical or different substituents from the group consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximinomethyl, 1-methoximinoethyl, nitro and cyano, or represents phenylalkenyl having 2 to 4 carbon atoms in the alkenyl moiety, where the phenyl moiety may be mono- to trisubstituted by identical or different substituents from the group consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximinomethyl, 1-methoximinoethyl, nitro and cyano, or represents phenoxyalkyl having 1 to 4 carbon atoms in the straight-chain or branched oxyalkyl moiety, where the phenyl moiety may be mono- to trisubstituted by identical or different substituents from the group consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximinomethyl, 1-methoximinoethyl, nitro and cyano, or represents phenyl which may be mono- to trisubstituted by identical or different substituents from the group consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximinomethyl, 1-methoximinoethyl, nitro and cyano, or represents pyrazolyl, imidazolyl, 1,2,4-triazolyl, pyrrolyl, furanyl, thienyl, thiazolyl, oxazolyl, pyridinyl, pyrimidinyl, triazinyl, quinolinyl, isoquinolinyl, quinazolinyl, indolyl, benzothienyl, benzofuranyl, benzothiazolyl or benzimidazolyl, where each of these radicals may be mono- to trisubstituted by identical or different substituents from the group consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, chlorodifluoromethylthio, hydroxymethyl, hydroxyethyl, hydroxyalkinyl having 4 to 6 carbon atoms, methoxycarbonyl, ethoxycarbonyl, methoximinomethyl, 1-methoximinoethyl, nitro, cyano, formyl, dimethyoxymethyl, acetyl and propionyl.

Very particular preference is given to using hydrazine derivatives of the formula (II) in which $R^1$ represents n-propyl, isopropyl, n-butyl, i-butyl, sec-butyl or tert-butyl, where these radicals may be mono- to tetrasubstituted by identical or different substituents from the group consisting of fluorine, chlorine, bromine, methoxy, ethoxy, propoxy, isopropoxy, methoximino, ethoximino, cyclopropyl, cyclobutyl, cyclopentyl and cyclohexyl, or represents straight-chain or branched alkenyl having 2 to 5 carbon atoms, where each of these radicals may be mono- to trisubstituted by identical or different substituents from the group consisting of fluorine, chlorine, bromine, methoxy, ethoxy, propoxy, isopropoxy, cyclopropyl, cyclobutyl, cyclopentyl and cyclohexyl, or represents 1-methyl-cyclohexyl, cyclohexyl, 1-chloro-cyclopropyl, 1-fluoro-cyclopropyl, 1-methyl-cyclopropyl, 1-cyano-cyclopropyl, cyclopropyl, 1-methyl-cyclopentyl or 1-ethyl-cyclopentyl, or represents phenylalkyl having 1 or 2 carbon atoms in the straight-chain or branched alkyl moiety, where the phenyl moiety may be mono- to trisubstituted by identical or different substituents from the group consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximinomethyl, 1-methoximinoethyl, nitro and cyano, or represents phenylalkenyl having 2 to 4 carbon atoms in the alkenyl moiety, where the phenyl moiety may be mono- to trisubstituted by identical or different substituents from the group consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximinomethyl, I-methoximinoethyl, nitro and cyano, or represents phenoxyalkyl having 1 to 4 carbon atoms in the straight-chain or branched oxyalkyl moiety, where the phenyl moiety may be mono- to trisubstituted by identical or different substituents from the group consisting of fluorine, chlorine, bromine, methyl, ethyl, tert-butyl, methoxy, ethoxy, methylthio, trifluoromethyl, trifluoromethoxy, trifluormethylthio, chlorodifluoromethoxy, difluoromethoxy, chlorodifluoromethylthio, methoxycarbonyl, ethoxycarbonyl, methoximinomethyl, 1-methoximinoethyl, nitro and cyano, or represents phenyl which may be mono- to trisubstituted by identical or different substituents from the group consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximinomethyl, 1-methoximinoethyl, nitro and cyano, or represents pyrazolyl, imidazolyl, 1,2,4-triazolyl, pyrrolyl, furanyl, thienyl, thiazolyl, oxazolyl, pyridinyl, pyrimidinyl, triazinyl, quinolinyl, isoquinolinyl, quinazolinyl, indolyl, benzothienyl, benzofuranyl, benzothiazolyl or benzimidazolyl, where each of these radicals may be mono- to trisubstituted by identical or different substituents from the group consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, chlorodifluoromethylthio, hydroxymethyl, hydroxyethyl, hydroxyalkinyl having 4 to 6 carbon atoms, methoxycarbonyl, ethoxycarbonyl, methoximinomethyl, 1-methoximinoethyl, nitro, cyano, formyl, dimethoxymethyl, acetyl and propionyl, and $R^2$ represents n-propyl, isopropyl, n-butyl, i-butyl, sec-butyl or tert-butyl, where these radicals may be mono- to tetrasubstituted by identical or different substituents from the group consisting of fluorine, chlorine, bromine, methoxy, ethoxy, propoxy, isopropoxy, methoximino, ethoximino, cyclopropyl, cyclobutyl, cyclopentyl and cyclohexyl, or represents straight-chain or branched alkenyl having 2 to 5 carbon atoms, where each of these radicals may be mono- to trisubstituted by identical or different substituents from the group consisting of fluorine, chlorine, bromine, methoxy, ethoxy, propoxy, isopropoxy, cyclopropyl, cyclobutyl, cyclopentyl and cyclohexyl, or represents 1-methyl-cyclohexyl, cyclohexyl, 1-chloro-cyclopropyl, 1-fluoro-cyclopropyl, 1-methyl-cyclopropyl, 1-cyano-cyclopropyl, cyclopropyl, 1-methyl-cyclopentyl or 1-ethyl-cyclopentyl, or represents phenylalkyl having 1 or 2 carbon atoms in the straight-chain or branched alkyl moiety, where the phenyl moiety may be mono- to trisubstituted by identical or different substituents from the group consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximinomethyl, 1-methoximinoethyl, nitro and cyano, or represents phenylalkenyl having 2 to 4 carbon atoms in the alkenyl moiety, where the phenyl moiety may be mono- to trisubstituted by identical or different substituents from the group consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximinomethyl, 1-methoximinoethyl, nitro and cyano, or represents phenoxyalkyl having 1 to 4 carbon atoms in the straight-chain or branched oxyalkyl moiety, where the phenyl moiety may be mono- to trisubstituted by identical or different substituents from the group consisting of fluorine, chlorine, bromine methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximinomethyl, 1-methoximinoethyl, nitro and cyano, or represents phenyl which may be mono- to trisubstituted by identical or different substituents from the group consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximinomethyl, 1-methoximinoethyl, nitro and cyano, or represents pyrazolyl, imidazolyl, 1,2,4-triazolyl, pyrrolyl, furanyl, thienyl, thiazolyl, oxazolyl, pyridinyl, pyrimidinyl, triazinyl, quinolinyl, isoquinolinyl, quinazolinyl, indolyl, benzothienyl, benzofuranyl, benzothiazolyl or benzimidazolyl, where each of these radicals may be mono- to trisubstituted by identical or different substituents from the group consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, chlorodifluoromethylthio, hydroxymethyl, hydroxyethyl, hydroxyalkinyl having 4 to 6 carbon atoms, methoxycarbonyl, ethoxycarbonyl, methoximinomethyl, 1-methoximinoethyl, nitro, cyano, formyl, dimethyoxymethyl, acetyl and/ propionyl.

The hydrazine derivatives of the formula (H) are known or can be prepared by processes known in principle (cf. DE-A-40 30 039).

Thus, hydrazine derivatives of the formula (II) are obtained by reacting 1-chloro-2-hydroxyethane derivatives of the formula

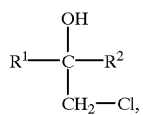

(VI)

in which $R^1$ and $R^2$ are each as defined above, in the presence of an acid binder, such as potassium tert-butoxide, sodium methoxide or potassium carbonate, and in the presence of a diluent, such as dimethylformamide, methanol, n-butanol, tetrahydrofuran or methyl tert-butyl ether, at temperatures between 20° C. and 60° C., and reacting the resulting oxirane derivatives of the formula

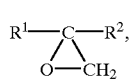

(VII)

in which $R^1$ and $R^2$ are each as defined above with hydrazine hydrate, if appropriate in the presence of a diluent, such as methanol, n-butanol, tetrahydrofuran, methyl tert-butyl ether, dioxane or nitriles, such as acetonitrile, at temperatures between 30° C. and 120° C.

Particular preference is given to reacting the 1-chloro-2-hydroxy-ethane derivatives of the formula (VI) with excess hydrazine hydrate, acting here both as reactant and as base and diluent.

The 1-chloro-2-hydroxy-ethane derivatives of the formula (VI) are known or can be prepared by processes known in principle (cf. DE-A 40 30 039 and EP-A 0 297 345).

The formaldehyde required as reaction component for carrying out the first step of the process according to the invention can be employed as paraformaldehyde, as gaseous formaldehyde or else as formalin solution (=aqueous formaldehyde solution).

Furthermore, thiocyanates of the formula (III) are employed as reaction components when carrying out the first step of the process according to the invention. The thiocyanates of the formula (III) are known.

Suitable diluents for carrying out the first step of the process according to the invention are all inert organic solvents which are customary for such reactions. Preference is given to using alcohols, such as n-butanol and tert-butanol, furthermore ethers such as dioxane and methyl tert-butyl ether, moreover nitriles, such as acetonitrile, and hydrocarbons, such as toluene or chlorobenzene, in each case if appropriate as a mixture with water.

Suitable acids for carrying out the first step of the process according to the invention are all customary inorganic and organic acids. Preference is given to using hydrochloric acid, sulphuric acid, p-toluenesulphonic acid and also sodium hydrogen sulphate in the presence of water.

Both the first and the second step of the process according to the invention are generally carried out under atmospheric pressure. However, it is also possible to operate under elevated pressure or, if no gaseous components participate in the reaction, under reduced pressure.

When carrying out the first step of the process according to the invention, generally from 1 to 2 mol of formaldehyde and from 1 to 2 mol of thiocyanate of the formula (III) and, if appropriate, an equivalent amount of acid or sodium hydrogen sulphate and water, where the water may also be present in excess, are employed per mole of hydrazine derivative of the formula (II). Work-up is carried out by customary methods. If the reaction is carried out in the absence of water, the reaction mixture is, if appropriate after prior dilution with an organic solvent which is sparingly water-miscible, generally washed with aqueous-alkaline solution, and the organic phase is dried and concentrated. If the reaction is carried out in the presence of water and in the presence of sodium hydrogen sulphate, the reaction mixture is generally diluted with an organic solvent which is sparingly water-miscible, filtered and concentrated under reduced pressure. Any impurities which may then still be present can be removed by customary methods, such as recrystallization or chromatography.

The formula (IV) provides a general definition of the triazolidinethiones required as starting materials for carrying out the second step of the process according to the invention. II this formula, $R^1$ and $R^2$ preferably have those meanings which have already been mentioned in connection with the description of the hydrazine derivatives of the formula (II) as being preferred for these radicals.

The triazolidinethiones of the formula (IV) have hitherto not been disclosed. They can be prepared by the reaction of the first step of the process according to the invention.

Preferred oxidizing agents for carrying out the second step of the process according to the invention according to variant (cc) are oxygen, sulphur and potassium peroxide. If the oxidizing agent used is oxygen, this is preferably added in the form of air.

Preferred catalyst for carrying out the second step of the process according to the invention according to variant ((α) is a mixture of potassium hydroxide and sulphur powder. This catalyst is preferably employed when the oxidizing agent used is oxygen.

Suitable diluents for carrying out the second step of the process according to the invention according to variant (α) are all inert organic solvents which are customary for such reactions. Preference is given to using aliphatic, cycloaliphatic and aromatic hydrocarbons, such as pentane, hexane, cyclohexane, benzene, toluene and xylene, furthermore ethers, such as methyl tert-butyl ether, and also esters, such as n-butyl acetate.

When carrying out the second step of the process according to the invention according to variant (α), the reaction temperatures can be varied within a relatively wide range. In general, the reaction is carried out at temperatures between 0° C. and 120° C. If the oxidizing agent used is oxygen, the reaction is preferably carried out at temperatures between 20° C. and 80° C. If the oxidizing agent used is sulphur, the reaction is preferably carried out at temperatures between 50° C. and 1 10C. If the oxidizing agent used is potassium peroxide, the reaction is preferably carried out at temperatures between 20° C. and 80° C.

When carrying out the second step of the process according to the invention according to variant (α), in general an excess of oxidizing agent is used per mole of triazolidinethione of the formula (IV). If the oxidizing agent used is sulphur or potassium peroxide, preference is given to using from 1.5 to 2 mol of oxidizing agent per mole of triazolidinethione of the formula (IV). If the oxidizing agent used is oxygen in the form of air, preference is given to passing a stream of air through the reaction mixture until the reaction has ended. Work-up is in each case carried out by customary methods. In general, the reaction mixture is, if appropriate after prior dilution with an organic solvent which is sparingly water-miscible, extracted with aqueous salt solution, and the organic phase is dried and concentrated. Any impurities which may then still be present can be removed by customary methods, such as recrystallization or chromatography. However, it is also possible to isolate the product as the potassium salt and then to liberate the product by addition of acid.

When carrying out the second step of the process according to the invention according to variant (β), the reaction temperatures can likewise be varied within a certain range. In general, the reaction is carried out at temperatures between 50° C. and 100° C.

When carrying out the second step of the process according to the invention according to variant (β), formic acid acts both as reaction component and as diluent. Thus, in general a high excess of formic acid is employed per mole of triazolidinethione of the formula (IV). Once more, work-up is carried out by customary methods. In general, the reaction mixture is concentrated under reduced pressure and the desired product is isolated from the residue that remains by recrystallization and/or by chromatographic means.

In a particular variant, the process according to the invention can be carried out such that 1-chloro-2-hydroxyethane derivatives of the formula (VI) are reacted with hydrazine hydrate and the resulting hydrazine derivatives of the formula (II) are then reacted further without prior isolation. Thus, triazolinethiones of the formula (I) can also be prepared by reacting 1 -chloro-2-hydroxy-ethane derivatives of the formula (VI)

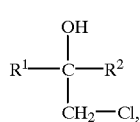

in which

R$^1$ and R$^2$ are each as defined above with hydrazine hydrate, if appropriate in the presence of a diluent, reacting the resulting hydrazine derivatives of the formula (II)

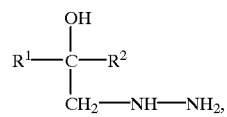

in which

R$^1$ and R$^2$ are each as defined above without prior isolation with formaldehyde and thiocyanate of the formula

X—SCN (III), in which

X represents sodium, potassium or ammonium, in the presence of a diluent and if appropriate in the presence of an acid, and reacting the resulting triazolidinethiones of the formula (IV)

in which

R$^1$ and R$^2$ arc each as defined above either

α) with oxidizing agents, if appropriate in the presence of a catalyst and in the presence of a diluent, or β) with formic acid of the formula

HCOOH (V).

Suitable diluents for carrying out the first step of this variant of the process according to the invention are all customary inert organic solvents. Preference is given to using alcohols, such as n-butanol, and ethers, such as dioxane or methyl tert-butyl ether, and also nitriles, such as acetonitrile. However, it is also possible to carry out the reaction without additional solvent. In this case, hydrazine hydrate is employed in excess, so that it acts both as reaction component and as diluent.

When carrying out the first step of this variant of the process according to the invention, the reaction temperatures can be varied within a certain range. In general, the reaction is carried out at temperatures between 60° C. and 120° C., preferably between 70° C. and 100° C.

The first step of this variant of the process according to the invention is preferably carried out such that between 3 and 20 mol, particularly preferably between 4 and 15 mol, of hydrazine hydrate are employed per mole of 1-chloro-2-hydroxy-ethane derivative of the formula (VI), and the mixture is then diluted with an organic solvent which is sparingly water-miscible, such as methyl tert-butyl ether, the aqueous phase is separated off, and the organic phase is washed and dried and then used for the subsequent reactions without any further work-up.

The other steps of this variant of the process according to the invention are carried out in the manner described above.

The triazolinethione derivatives preparable according to the invention can be present in the "thiono" form of the formula

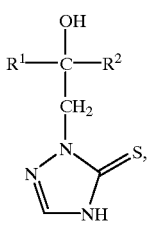

(I)

or in the tautomeric "mercapto" form of the formula

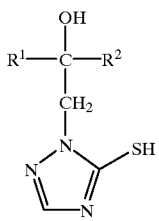

(Ia)

For the sake of simplicity, only the "thiono" form is shown in each case.

The triazolinethione derivatives preparable according to the invention are known as active compounds having microbicidal, in particular fungicidal, properties (cf. WO A 96-16048).

The practice of the process according to the invention is illustrated by the examples below.

PREPARATION EXAMPLES

Example 1

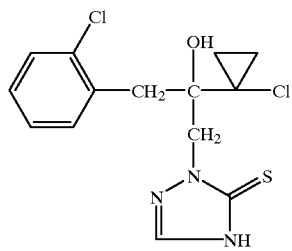

a) Preparation of the compound of the formula

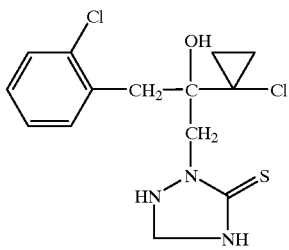

With stirring, a mixture of 5.48 g (20 mmol) of [2-(1-chloro-cycloprop-1-yl)-3-(2-chlorophenyl)-2-hydroxy]-propyl-1-hydrazine, 40 ml of methyl tert-butyl ether, 0.9 g (30 mm-ol) of paraformaldehyde and 1.84 g (24 mmol) of ammonium thiocyanate is heated at 60° C. for 3 hours. After cooling to room temperature, the reaction mixture is diluted with methyl tert-butyl ether and washed with saturated aqueous sodium carbonate solution. The organic phase is dried over sodium sulphate, filtered and concentrated tinder reduced pressure. This gives 6.1 g of a product which, according to HPLC analysis, comprises 86.9% of 2-(1-chloro-cycloprop-1-yl)-1-(2-chlorophenyl)-2-hydroxy-3-(1, 2,4-triazolidine-5-thiono-1-yl)-propane. After addition of a little dichloromethane, 2-(1-chloro-cycloprop-1-yl)-1-(2-chloro-phenyl)-2-hydroxy-3-(1,2,4-triazolidine-5-thiono-1-yl)-propane precipitates out in the form of a crystalline solid.

Melting point: 152–154° C. $^1$H NMR spectrum (CDCl$_3$, TMS, 250 MHz): δ=0.8–1.3 (m,3H); 3.1 (d, J=14 Hz, 1H); 3.65 (d, J=14 Hz, 1H); 4.2 (s,2H); 4.45–4.65 (m,3H); 5.1 (t, NH); 7.15–7.6 (m,4H) ppm b) Preparation of the compound of the formula

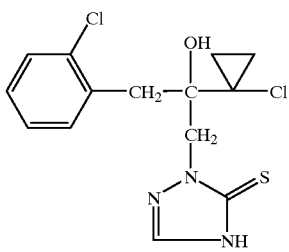

With stirring, a stream of air is passed for 3.5 hours over a mixture of 1.72 g (5 mmol) of 2-(1 -chloro-cycloprop-1-yl)-1-(2-chloro-phenyl)-2-hydroxy-3-(1,2,4-triazolidine-5-thiono-1-yl)-propane, 10 ml of absolute toluene, 0.34 g (6 mmol) of potassium hydroxide powder and 10 mg of sulphur powder which had been heated to 70° C. The progress of the reaction is monitored by HPLC analysis. After cooling to room temperature, the reaction mixture is diluted with methyl tert-butyl ether and washed repeatedly with saturated aqueous ammonium chloride solution. The organic phase is dried over sodium sulphate, filtered and concentrated under reduced pressure. This gives 2.2 g of a product which, according to HPLC analysis, comprises 71% of 2-(1-chloro-cycloprop-1-yl)-1-(2-chloro-phenyl)-3-(4,5-dihydro-1,2,4-triazole-5-thiono-1-yl)-propan-2-ol. After recrystallization from toluene, the substance has a melting point of from 136 to 138° C.

Example 2

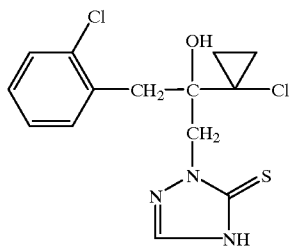

a) Preparation of the compound of the formula

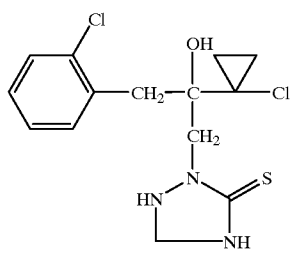

With stirring, a mixture of 2.78 g (10 mmol) of 3-chloro-2-(1-chloro-cycloprop-1-yl)-1-(2-chloro-phenyl)-propan-2-ol and 4.9 ml (100 mmol) of hydrazine hydrate is heated at 80° C. for 3 hours. The reaction mixture is then cooled to 20° C., 15 ml of methyl tert-butyl ether are added and the aqueous phase is separated off. The organic phase is washed once with 5 ml of water and then dried over 1 g of sodium sulphate. The reaction mixture is then filtered, admixed with 0.3 g (10 mmol) of paraformaldehyde and 0.76 g (20 mmol) of ammonium thiocyanate and heated with stirring at from 55 to 60° C. for 3 hours. The mixture is allowed to cool to room temperature, admixed with methyl tert-butyl ether and washed three times with saturated aqueous ammonium chloride solution. The organic phase is dried over sodium sulphate, filtered and concentrated under reduced pressure. This gives 2.4 g of a product which, according to HPLC analysis, comprises 68.3% of 2-(1-chloro-cycloprop-1-yl)-1-(2-chloro-phenyl)-2-hydroxy-3-(1,2,4-triazolidine-5-thiono-1-yl)-propane. After addition of a little dichloromethane, 2-(1-chloro-cycloprop-1-yl)- 1-(2-chloro-phenyl)-2-hydroxy-3-(1,2,4-triazolidine-5-thiono-1-yl)-propane precipitates out in the form of a crystalline solid.

Melting point: 152–154° C.

b) Preparation of the compound of the formula

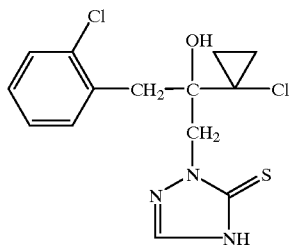

With stirring, a mixture of 1.71 g (5 mmol) of 2-(1-chloro-cycloprop-1-yl)-1-(2-chloro-phenyl)-2-hydroxy-3-(1,2,4-triazolidine-5-thiono-1-yl)-propane, 12.5 ml of n-butyl acetate and 0.25 g (7.5 mmol) of sulphur powder is heated at 100° C. for 9 hours, during which the progress of the reaction is monitored by HPLC analysis. The reaction mixture is then cooled to room temperature, diluted with methyl tert-butyl ether and washed repeatedly with saturated aqueous ammonium chloride solution. The organic phase is dried over sodium sulphate, filtered and concentrated under reduced pressure. This gives 2.5 g of a product which, according to HPLC analysis, comprises 72.2% of 2-(1-chloro-cycloprop-1-yl)-1-(2-chloro-phenyl)-3-(4,5-dihydro-1,2,4-triazole-5-thiono-1-yl)-propan-2-ol. After recrystallization from toluene, the substance has a melting point of from 137 to 138° C.

Example 3

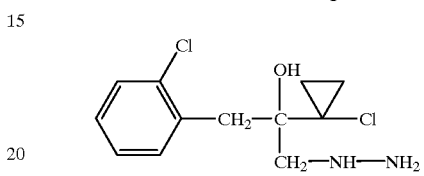

Under an atmosphere of nitrogen and with stirring, a mixture of 27.8 g (0.1 mol) of 3-chloro-2-(1-chloro-cycloprop-1-yl)-1-(2-chloro-phenyl)-propan-2-ol and 48.5 ml (1 mol) of hydrazine hydrate is heated at 100° C. for 5 hours. After cooling of the two-phase system to room temperature, the hydrazine phase is decanted off and the residue is washed once with 20 ml of water. This gives 25.9 g of a product which, according to gaschromatographic analysis, comprises 86.8% of 2-(1-chloro-cycloprop-1-yl)-3-(2-chloro-phenyl)-2-hydroxy-propyl-1-hydrazine. Accordingly, the calculated yield is 94.5% of theory. Recrystallization of the crude product from acetonitrile gives 2-(1-chloro-cycloprop-1-yl)-3-(2-chloro-phenyl)-2-hydroxy-propyl-1-hydrazine in the form of a solid of melting point 86° C. to 88° C.

$^1$H NMR spectrum (400 MHz, CDCl$_3$, TMS): δ=0.8–1.05 (m,3H); 1.25 (m,1H); 2.7 (d,1H); 2.95 (d,1H); 3.45 (d,1H); 3.6 (d,1H); 2.8–3.5 (3H,NH); 4.6 (1H,OH); 7.1–7.5 (m,4H) ppm

Example 4

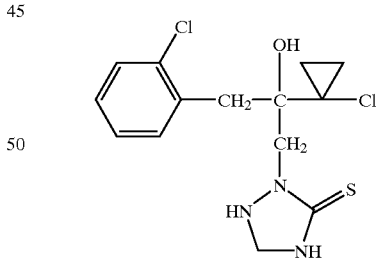

At 0° C. and under an atmosphere of nitrogen, a mixture of 2.74 g (10 mmol) of [2-(1-chloro-cycloprop-1-yl)-3-(2-chlorophenyl)-2-hydroxy]-propyl-1-hydrazine (which had been recrystallized from acetonitrile), 10 ml of toluene and 0.5 ml of water is initially charged. With stirring at 0° C., formaldehyde, obtained by prior depolymerization of 0.36 g (12 mmol) of paraformaldehyde at about 150° C., is passed in gaseous form together with a stream of nitrogen into this mixture. After the addition has ended, stirring is continued at 20° C. for 30 minutes, and the mixture is then admixed with 0.82 g (10 mmol) of sodium thiocyanate and 1.2 g (10 mmol) of sodium hydrogen sulphate. The resulting reaction mixture is stirred at 20° C. for 2 hours and subsequently diluted with 100 ml of dichloromethane. The solid is filtered off and the liquid organic phase is concentrated under reduced pressure. This gives 3.28 g of a product which, according to HPLC analysis, comprises 98.6% of 2-(1-chloro-cycloprop-1-yl)-(2-chloro-phenyl)-2-hydroxy-3-(1,2,4-triazolidine-5-thiono-1-yl)-propane. Accordingly, the calculated yield is 95% of theory.

Melting point: 157–158° C.

Example 5

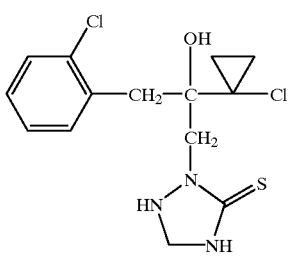

At 0° C. and under an atmosphere of nitrogen, a mixture of 2.74 g (10 mmol) of [2-(1-chloro-cycloprop-1-yl)-3-(2-chlorophenyl)-2-hydroxy]-propyl-1-hydrazine (which had been recrystallized from acetonitrile) and 10 ml of toluene is admixed with stirring with 0.74 ml (10 mmol) of a 40% strength formalin solution. After the addition has ended, the mixture is stirred at 20° C. for 30 minutes and then admixed with 0.82 g (10 mmol) of sodium thiocyanate and 1.2 g (10 mmol) of sodium hydrogen sulphate. The reaction mixture is stirred at 20° C. for 2 hours and subsequently diluted with 100 ml of dichloromethane. The solid is filtered off and the liquid organic phase is concentrated under reduced pressure. This gives 3.3 g of a product which, according to HPLC analysis, comprises 93.9% of 2-(1-chloro-cycloprop- 1-yl)-1-(2-chlorophenyl)-2-hydroxy-3-(1,2,4-triazolidine-5-thiono-1-yl)-propane. Accordingly, the calculated yield is 90.2% of theory.

Melting point: 154–155° C.

Example 6

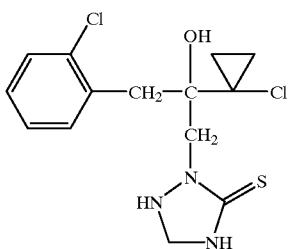

At 0° C. and under an atmosphere of nitrogen, a mixture of 2.74 g (10 mmol) of [2-(1-chloro-cycloprop- -yl)-3-(2-chlorophenyl)-2-hyxroxy]-propyl-1-hydrazine (which had been recrystallized from acetonitrile) and 10 ml of toluene is successively admixed with stirring with 1.2 g (10 mmol) of sodium hydrogen sulphate, 0.74 ml (10 mmol) of a 40% strength formalin solution and 0.82 g (10 mmol) of sodium thiocyanate. After the addition has ended, the mixture is stirred at 20° C. for 2 hours and then diluted with 100 ml of dichloromethane. The solid is filtered off and the liquid organic phase is concentrated under reduced pressure. This gives 3.4 g of a product which, according to HPLC analysis, comprises 83.1% of 2-(1-chloro-cycloprop-1-yl)-1-(2-chlorophenyl)-2-hydroxy-3-(1,2,4-triazolidine-5-thiono-1-yl)-propane. Accordingly, the calculated yield is 83% of theory.

Melting point: 136–138° C.

COMPARATIVE EXAMPLES

Example A

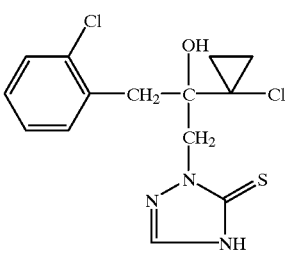

At −20° C., a mixture of 3.12 g (10 mmol) of 2-(-chloro-cycloprop-1-yl)-1-(2-chlorophenyl)-3-(1,2,4-triazol-1-yl)-propan-2-ol and 45 ml of absolute tetrahydrofuran is admixed with 8.4 ml (21 mmol) of n-butyl-lithium in hexane and stirred at 0° C. for 30 minutes. The reaction mixture is then cooled to −70° C., admixed with 0.32 g of (10 mmol) of sulphur powder and stirred at −70° C. for 30 minutes. The mixture is warmed to −10° C., admixed with ice-water and adjusted to pH 5 by addition of dilute sulphuric acid. The mixture is extracted repeatedly with ethyl acetate, and the combined organic phases are dried over sodium sulphate and concentrated under reduced pressure. In this manner, 3.2 g of a product which, according to gaschromatographic analysis, comprises 95% of 2-(1-chloro-cycloprop-1-yl)-1-(2-chloro-phenyl)-3-(4,5-dihydro-1,2,4-triazole-5-thiono-1-yl)-propan-3-ol are obtained. After recrystallization from toluene, the substance has a melting point of from 138° C. to 139° C.

Example B

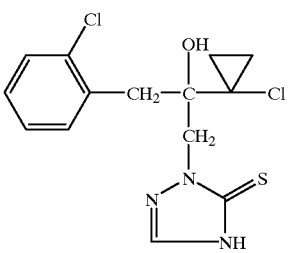

With stirring, a mixture of 3.12 g (10 mmol) of 2-(1-chloro-cycloprop-1-yl)-1-(2-chloro-phenyl)-3-(1,2,4-triazol-1-yl)-propan-2-ol, 0.96 g (30 mmol) of sulphur powder and 20 ml of absolute N-methyl-pyrrolidone is heated at 200° C. for 44 hours. The reaction mixture is then concentrated under reduced pressure (0.2 mbar). The resulting crude product (3.1 g) is recrystallized from toluene. In this manner, 0.7 g (20% of theory) of 2-(1-chloro-cycloprop-1-yl)-1-(2-chloro-phenyl)-3-(4,5-dihydro-1,2,4-triazole-5-thiono-1-yl)-propan-2-ol is obtained in the form of a solid which melts at 138–139° C.

What is claimed is:

1. A process for preparing a triazolinethione derivative of the formula

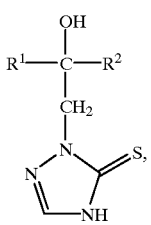     (I)

in which
R$^1$ and R$^2$ are identical or different and each represents optionally substituted alkyl, optionally substituted alkenyl, optionally substituted cycloalkyl, optionally substituted aralkyl, optionally substituted aralkenyl, optionally substituted aroxyalkyl, optionally substituted aryl or optionally substituted heteroaryl, comprising reacting
a) in a first step a hydrazine derivative of the formula

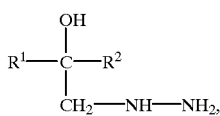     (II)

in which
R$^1$ and R$^2$ are each as defined above with formaldehyde and a thiocyanate of the formula

 X—SCN     (III), in which
X represents sodium, potassium or ammonium, in the presence of a diluent, and reacting
b) the resulting triazolidinethione of the formula

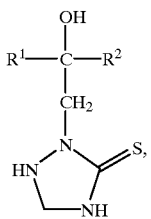     (IV)

in which
R$^1$ and R$^2$ are each as defined above in a second step, either

α) with an oxidizing agent in the presence of a diluent, or alternatively

β) with formic acid of the formula

 HCOOH     (V).

2. The process according to claim 1, characterized in that the hydrazine derivative starting material used is 2-(1-chloro-cycloprop-1-yl)-3-(2-chloro-phenyl)-2-hydroxy-propyl-1-hydrazine having the formula

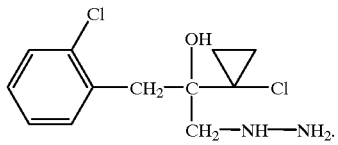

3. The process according to claim 1, characterized in that the formaldehyde used for carrying out the first step is paraformaldehyde, gaseous formaldehyde, or formalin solution.

4. The process according to claim 1, characterized in that the reaction component used for carrying out the first step is ammonium thiocyanate.

5. The process according to claim 1, characterized in that the reaction components used for carrying out the first step are sodium thiocyanate in the presence of an acid.

6. The process according to claim 1, characterized in that the reaction components used for carrying out the first step are sodium thiocyanate in the presence of sodium hydrogen sulphate and water.

7. The process according to claim 1, characterized in that the first step is carried out at temperatures between −20° C. and +100° C.

8. The process according to claim 1, characterized in that the second step according to variant ((α) is carried out at temperatures between 0° C. and 120° C.

9. The process according to claim 1, characterized in that the second step according to variant (β) is carried out at temperatures between 50° C. and 100° C.

* * * * *